(12) United States Patent
Takahashi

(10) Patent No.: US 7,298,485 B2
(45) Date of Patent: Nov. 20, 2007

(54) METHOD OF AND A DEVICE FOR MEASURING OPTICAL ABSORPTION CHARACTERISTICS OF A SAMPLE

(75) Inventor: Hiromi Takahashi, Koganei (JP)

(73) Assignee: System Instruments Co., Ltd., Tokyo (JP)

( * ) Notice: Subject to any disclaimer, the term of this patent is extended or adjusted under 35 U.S.C. 154(b) by 157 days.

(21) Appl. No.: 11/200,086

(22) Filed: Aug. 10, 2005

(65) Prior Publication Data

US 2006/0044560 A1    Mar. 2, 2006

(30) Foreign Application Priority Data

Aug. 24, 2004    (JP)   ............................. 2004-244032

(51) Int. Cl.
     *G01N 21/00*    (2006.01)
(52) U.S. Cl. ........................ 356/432; 356/436; 356/445
(58) Field of Classification Search ................ 356/436, 356/445, 447, 448; 250/339.11
See application file for complete search history.

(56) References Cited

U.S. PATENT DOCUMENTS

| 3,415,602 A | 12/1968 | Harrick |
| 2002/0126290 A1* | 9/2002 | Naya ........................... 356/445 |
| 2005/0007596 A1* | 1/2005 | Wilks et al. ................. 356/436 |

FOREIGN PATENT DOCUMENTS

| EP | 1 371 966 A | 12/2003 |
| JP | 7-12715 | 1/1995 |
| JP | 2000 111474 A | 4/2000 |

OTHER PUBLICATIONS

Villagran J C et al; "Simplified attenuated total reflection apparatus"; Review of Scientific Instruments< AIP; vol. 60; No. 6; Jun. 1, 1989; pp. 1201-1202, XP000035898.

* cited by examiner

*Primary Examiner*—Tarifur Chowdhury
*Assistant Examiner*—Jonathon D Cook
(74) *Attorney, Agent, or Firm*—Stites & Harbison PLLC; Ross F. Hunt, Jr.

(57) ABSTRACT

The device for measuring an optical absorption characteristic of a sample according to the present invention comprising a light source, a optical wave-guide having light input surface(s) and light output surface(s) that are opposite to each other, and a light reflecting surface on which a sample to be measured is disposed, through which the light passes and is reflected by a total reflection on the sample, one or more light transmitting means arranged between the light output surface of the optical wave-guide and the light input surface of the optical wave-guide so that the light is again entered into the optical wave-guide, and a processing device which receives the light re-exited from the optical wave-guide through the output surface and detects the optical absorption characteristics of the sample on the basis of the light received, whereby the light which passes through the optical wave-guide is conducted to the optical wave-guide again, the light is again entered the optical wave-guide, and the light is again reflected on the sample (FIG. 1).

13 Claims, 12 Drawing Sheets

(a)

(b)

METHOD OF AND A DEVICE FOR MEASURING OPTICAL ABSORPTION CHARACTERISTICS OF A SAMPLE

FIELD OF THE INVENTION

The present invention relates to a method of measuring optical absorption characteristics of a sample having a quantity available for measurement that is extremely small by using an optical wave-guide. The present invention also relates to a device for measuring the optical absorption characteristics of the sample having very small quantity by using the optical wave-guide.

BACKGROUND OF THE ART

There is known a method of measuring an optical absorption characteristics of a sample in which the method comprises conducting a light to the sample so that the light is reflected on the sample by a total reflection, receiving the light that was reflected on the sample, and detecting the optical absorption characteristic of the sample on the basis of the received light in order to specify at least any one of a condition of a target substance in the sample, a kind of a target substance in the sample, a concentration of the target substance in the sample, and an amount of a target substance in the sample on the basis of the optical absorption characteristics of the sample.

In the above-mentioned conventional measuring method, an optical wave-guide is used for reflecting the light reflected on the sample by the total reflection.

The conventional optical wave-guide includes a trapezoid body or a rectangular parallelepiped body, so that the light is reflected by the total reflection several times in the optical wave-guide.

In the FIG. 12(a), there is shown such a conventional optical wave-guide that includes the trapezoid body. As shown in FIG. 12(a), the optical wave-guide has a pair of a light input surface 31 and a light output surface 32 that are opposite to each other, and a pair of an upper reflecting surface 33 and a bottom reflecting surface 34 that are opposite to each other. On the bottom reflecting surface 34, the sample 35 to be measured is disposed.

A laser light or a white light from a light source not shown in the drawing is entered into the optical wave-guide through the input surface 31, and the light continuously is reflected by the total reflection on the upper reflecting surface 33 and the bottom reflecting surface 34. The light is reflected by the total reflection on the sample disposed on the bottom reflecting surface 34 several times so that the optical absorptions are produced through every total reflection. The optical absorption characteristics depend on the kind of the target substance in the sample. Therefore, it is possible to specify the condition of the target substance, the kind of the target substance, the concentration of the target substance and the amount of the target substance in the sample by detecting the optical absorption characteristics of the sample from the light that was reflected on the sample by the total reflection in the optical wave-guide and then exited from the optical wave-guide (Referring the Japanese patent No. 2807777). For example the optical absorption characteristics may be any one of an amount of the optical absorption, an optical absorption intensity, and an optical absorption spectrum.

The measurement sensitivity of the above mentioned measuring method depends on the number of the reflecting times. More specifically, if the number of the reflecting times increases, the measurement sensitivity also increases. Conversely, if the number of the reflecting times decreases, the measurement sensitivity also decreases. Therefore, in order to increase the measurement sensitivity it is necessary to lengthen the optical wave-guide, or to thin the optical wave-guide, so that the number of the reflecting times is increased.

However, there is a technical limit in thinning the optical wave-guide.

Therefore, to increase the measurement sensitivity, it is actually necessary to lengthen the optical wave-guide. However, there is a problem that a device of large size for measuring the optical absorption characteristics should be used, if the optical wave-guide is lengthened.

If the optical wave-guide is lengthened, the number of reflecting times increases as shown in FIG. 12(b). However the area of the reflecting surface also enlarges, so that the amount of the sample to be required for measurement increases. Because it is difficult to extract the any kind of the samples that include a specimen that only trace amount thereof can be prepared or available, there is a serious problem that it becomes difficult to measure such a specimen if the increased amount thereof is required for measurement.

It is an object of the present invention to solve the above-mentioned problems and provide a method of measuring an optical absorption characteristics of a sample and a device for measuring an optical absorption characteristics of a sample that the amount of the sample to be measured can be minimized and the number of a total reflection can be suitably set by using an optical wave-guide having a minimized size.

SUMMARY OF THE INVENTION

To achieve the above object, a method of measuring an optical absorption characteristics of a sample according to the present invention comprises conducting a light from a light source to a optical wave-guide that has light input surface(s) and light output surface(s) that are opposite to each other, and a reflecting surface on which a sample to be measured is disposed, through which the light passes and is reflected by a total reflection on the sample, transmitting the light exited from the optical wave-guide through the output surface thereof to the input surface of the optical wave-guide so that the light is again entered into the optical wave-guide at least one time, receiving the light re-exited from the optical wave-guide, and detecting the optical absorption characteristics of the sample on the basis of the light received.

A device for measuring an optical absorption characteristic of a sample according to the present invention comprises a light source, a optical wave-guide having light input surface(s) and light output surface(s) that are opposite to each other, and a light reflecting surface on which a sample to be measured is disposed, through which the light passes and is reflected by a total reflection on the sample, one or more light transmitting means arranged between the light output surface of the optical wave-guide and the light input surface of the optical wave-guide so that the light is again entered into the optical wave-guide, and a processing device which receives the light re-exited from the optical wave-guide through the output surface and detects the optical absorption characteristics of the sample on the basis of the light received, whereby the light which passes through the optical wave-guide is conducted to the optical wave-guide again, the light is again entered the optical wave-guide, and the light is again reflected on the sample.

THE BEST MODE FOR CARRYING OUT THE INVENTION

The mode for carrying out a method of and a device for measuring optical absorption characteristics of a sample according to the present invention will now be described with reference to several embodiments shown in attached drawings.

Figure 1:
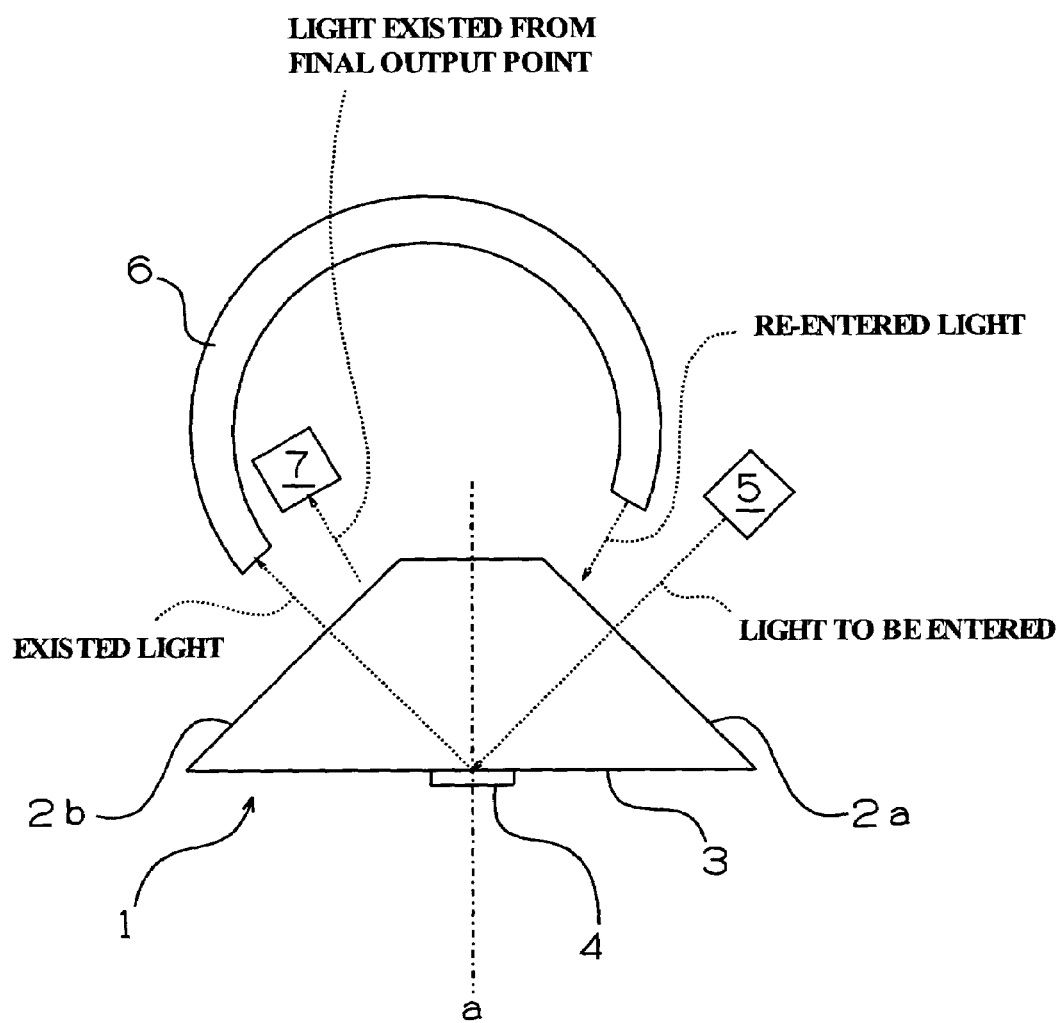
FIG. 1 is a schematic side view showing the first embodiment of the device for measuring the optical absorption characteristic of the sample according to the present invention.
Figure 2:
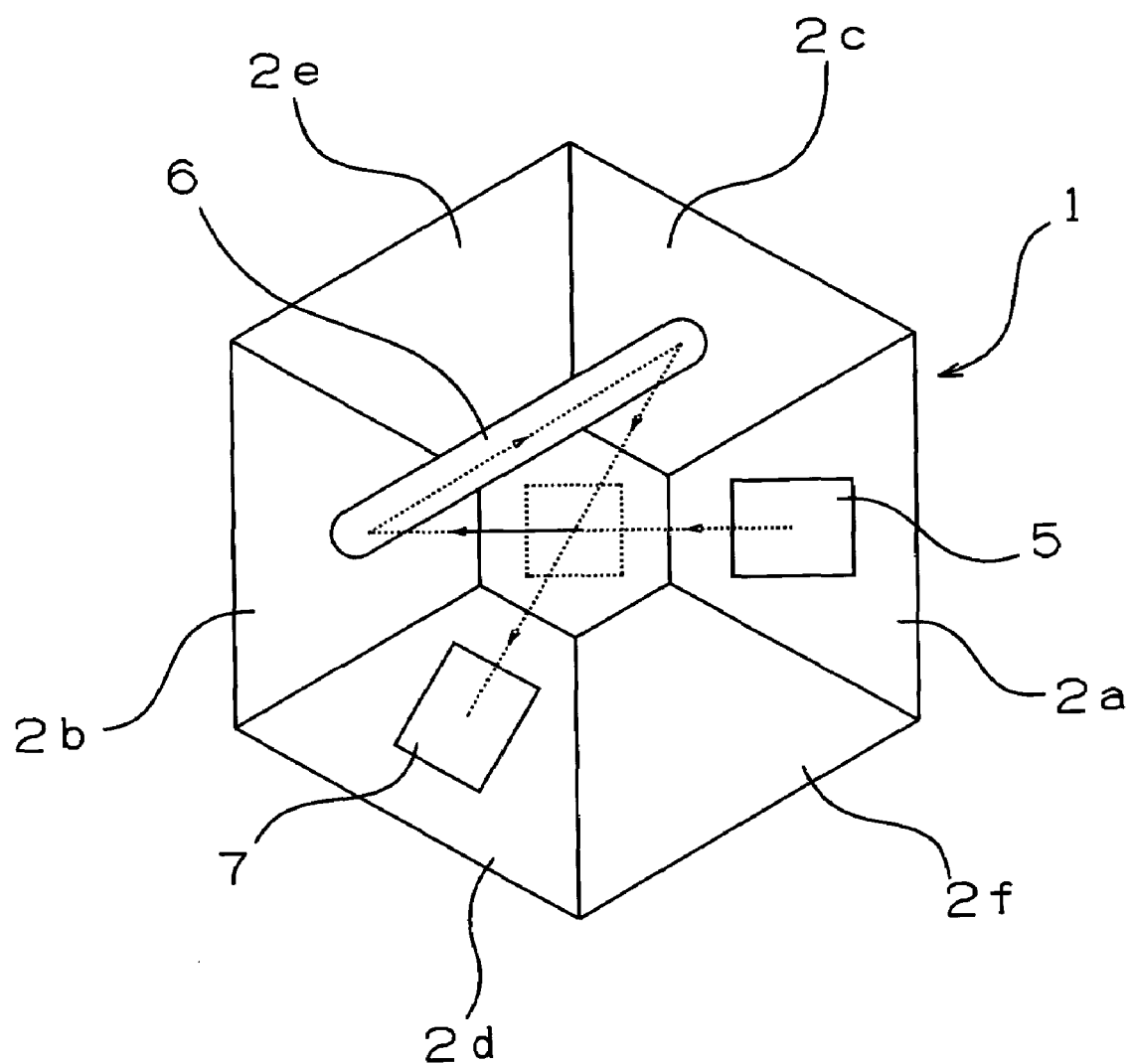
FIG. 2 is a schematic top view showing the device for measuring the optical absorption characteristics of the sample in FIG. 1.

FIG. 1 is a schematic side view of the first embodiment of a device for measuring optical absorption characteristics of sample according to the present invention in order to explain the principle of a method of measuring optical absorption characteristics of a sample according to the present invention. FIG. 2 is a schematic top view of the device shown in FIG. 1.

In the drawings, the numeral number 1 indicates an optical wave-guide. The optical wave-guide 1 is a truncated six-sided pyramid shape. The truncated six-sided pyramid shape optical wave-guide 1 has six side surfaces 2, i.e. three pairs of two side surfaces that are opposite to each other. In this embodiment, first pair of two side surfaces 2a and 2b that are opposite to each other are used as a first input surface 2a and a first output surface 2b and second pair of two side surfaces 2c and 2d that are opposite to each other are used as a second input surface 2c and a second output surface 2d. Said second output surface 2d is a final output surface in this embodiment.

The optical wave-guide 1 is made from transparent material having the refractive index by which the light may be guided by the total reflection through the optical wave-guide 1, for example, silica glass or high refractive index glass.

On a bottom surface (a reflecting surface) 3 of the optical wave-guide, a sample 4 being measured is disposed.

A light source 5 is arranged such that the laser light is entered into the optical wave-guide 1 through a predetermined first input point of the first input surface 2a. The light thus is entered into the optical wave-guide. The light is reflected by the total reflection on a predetermined reflecting point of the sample disposed on the reflecting surface 3. Then the laser light exits from the optical wave-guide 1 through a predetermined first output point of the first output surface 2b. The first input point is symmetrically opposite to the first output point with respect to a central axis "a" that perpendicularly extends through the predetermined reflecting point of the reflecting surface 3.

An optical fiber 6 is arranged as a light transmitting means that is provided between the first output surface 2b and the second input surface 2c. The optical fiber 6 receives the laser light exited from the optical wave-guide 1 through the first output point of the first output surface 2b, and transmits the light to a predetermined second input point of the second input surface 2c.

The light that is transmitted by the optical fiber 6 is again entered into the optical wave-guide through the second input point of the second input surface 2c. The re-entered light is again reflected by the total reflection on said reflecting point of the sample disposed on the reflecting surface 3. Then the light again exits from the optical wave-guide 1 through a second output point of the second output surface 2d, which is symmetrically opposite to the second input point of the second input surface 2c with respect to the central axis "a".

A processing device 7 is arranged such that it receives the laser light that was reflected two times by the total reflection on the sample in the optical wave-guide and then exited from the optical wave-guide 1 through the final output point (in this embodiment, the final output point is the second output point of the second output surface 2d). The processing device detects the optical absorption characteristics of the sample on the basis of the light, in order to specify the condition of the target substance, the kind of the target substance, the concentration of the target substance and the amount of the target substance in the sample. For example the optical absorption characteristics may be any one of an amount of the optical absorption, an optical absorption intensity, and an optical absorption spectrum. For example the optical absorption characteristics may be any one of an amount of the optical absorption, an optical absorption spectrum, and an optical absorption spectrum.

In the above embodiment, the light from the light source is reflected two times by the total reflection at the same reflecting point of the sample so that the measuring sensitivity is higher than that obtained in the conventional method using the same optical wave-guide as that of the above embodiment in which the light is reflected only one time by the total reflection at the one reflecting point of the sample.

In the above embodiment, the light is directly entered into the optical wave-guide from 1 the light source 5, the light exited from the optical wave-guide 1 is directly received by the optical fiber 6, and the light is directly re-entered into the optical wave-guide 1 from the optical fiber 6. However, said construction of the light source 5, the optical wave-guide 1 and the optical fiber 6 are not restricted to the above embodiment. If necessary, in order to efficiently transmit the light through the optical wave-guide and the optical fiber, a collective lens may be provided between the optical wave-guide 1 and the optical fiber 6, or an end face of the optical fiber 6 may be formed to a lens like shape.

Figure 3:
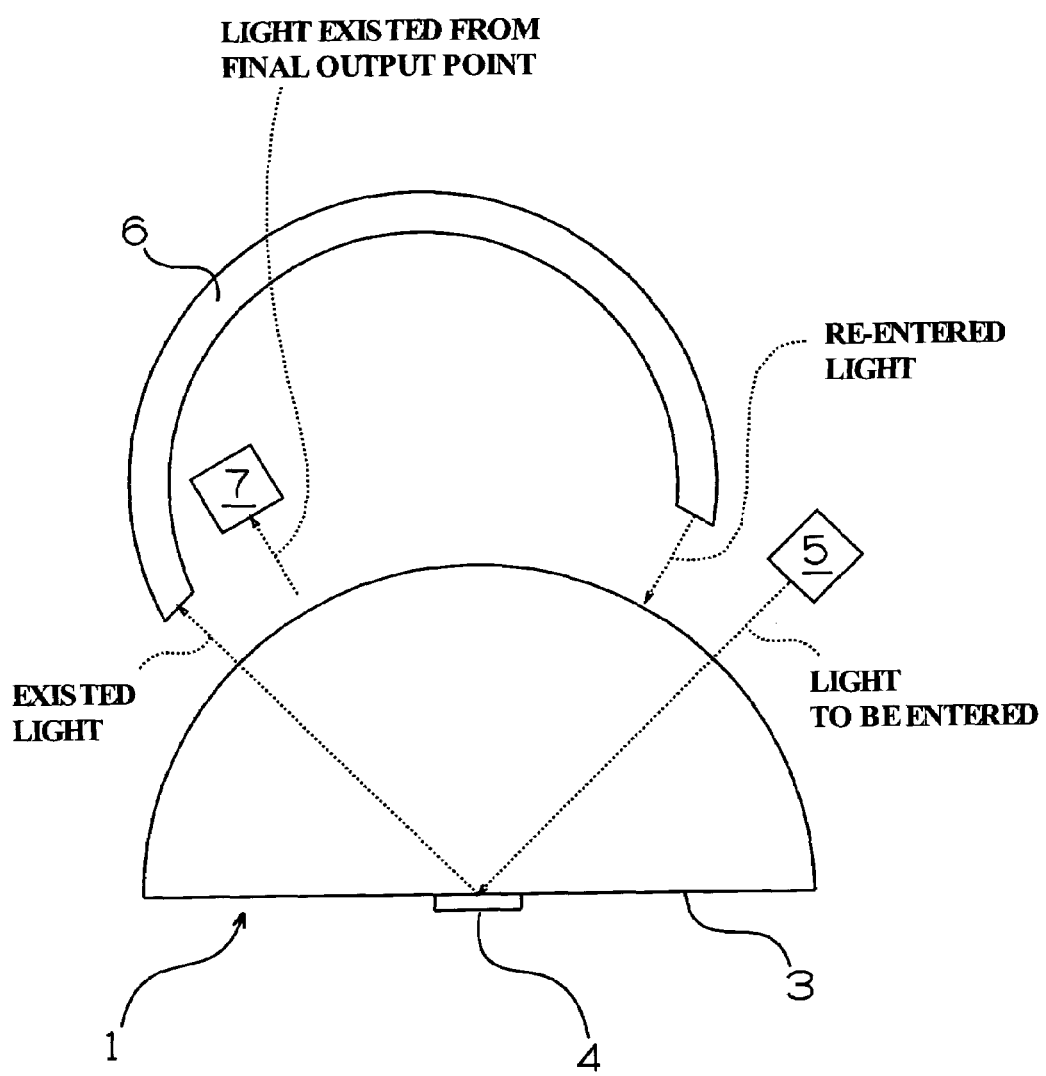
FIG. 3 is a schematic side view showing the second embodiment of the device for measuring the optical absorption characteristics of the sample according to the present invention.

In the above embodiment, the device for measuring the optical absorption characteristics is constructed such that the light is reflected two times by the total reflection on the sample in the optical wave-guide 1. However the number of light reflecting times is not restricted to the above embodiment. For example, in the above embodiment, an another optical fiber which may transmit the light exited from the optical wave-guide through the second output surface 2d to a third input surface 2e may be provided, so that the light is re-entered into the optical wave-guide two times and the light is reflected three time by the total reflection on the same reflecting point of the sample in the optical wave-guide 1. In this case, the processing device 7 must be arranged such that it receives the laser light exited from the optical wave-guide 1 through a third output point of a third output surface 2f, which is symmetrically opposite to the third input point of the third input surface 2e with respect to the central axis "a". On the basis of the this principle, the number of the light reflecting times may be arbitrarily increased with four times, five times, and more times by forming the optical wave-guide to a truncated eight-side pyramid shape or a truncated ten-side pyramid shape and increasing the number of pairs of two surfaces that are opposite to each other, which consists of the input surface and output surface of the optical wave-guide. Also as shown in FIG. 3, the optical wave-guide may be formed to the hemisphere shape. In this case, the light input point and the light output point may be determined without the side surface.

Further, with the optical wave-guide of the truncated shape mentioned in the illustrated embodiment, regardless of the truncated cone or pyramid shape, it is possible to use the optical wave-guide in a position reversed to that of the illustrated embodiment.

Figure 4:
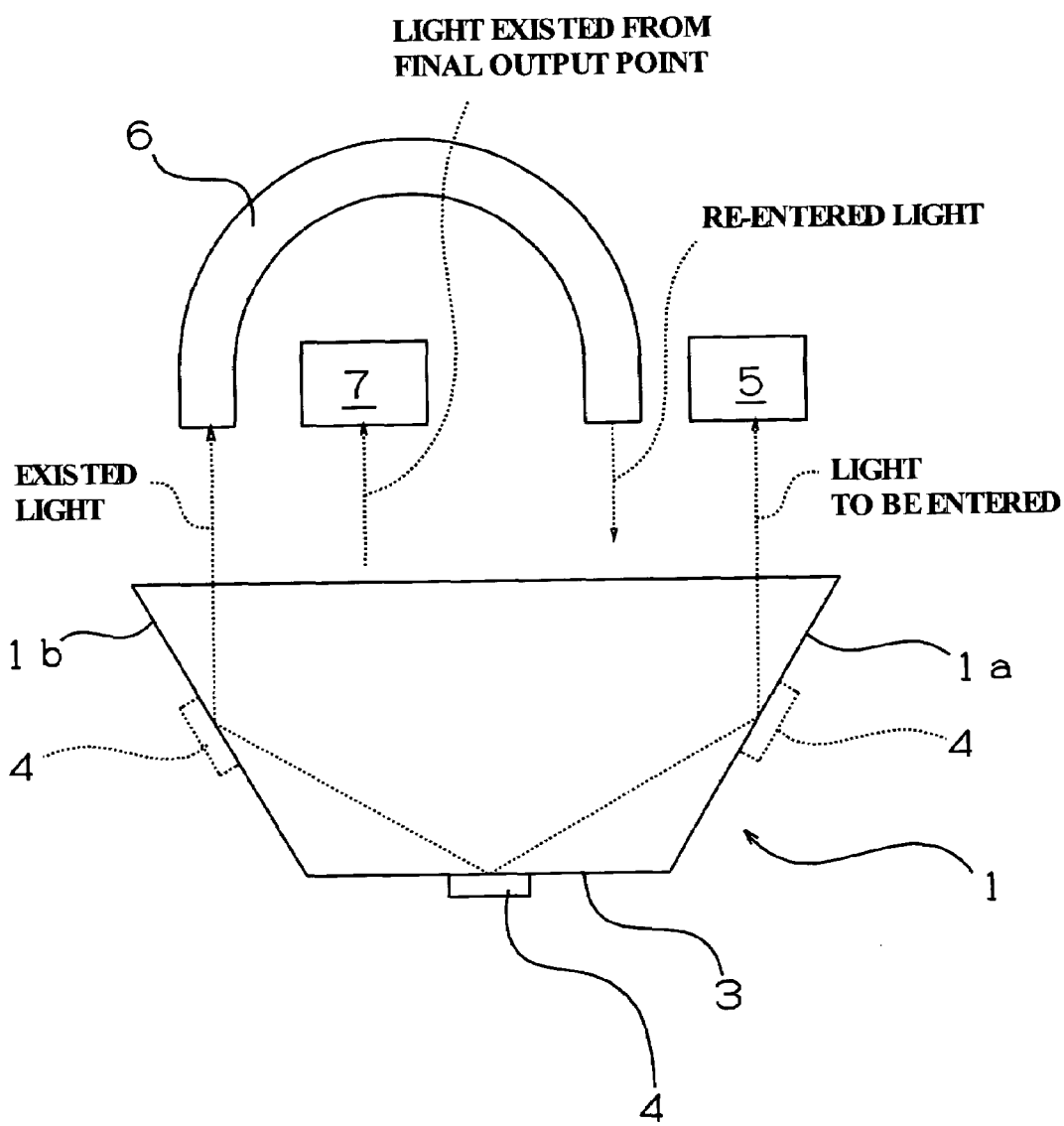
FIG. 4 is a schematic side view showing the third embodiment of the device for measuring the optical absorption characteristics of the sample according to the present invention.

FIG. 4 illustrates a case where the optical wave-guide of the truncated pyramid shape is used in a position reversed to that of the embodiment of FIG. 1. With the embodiment illustrated in FIG. 4, the incident light is reflected on the inclined surface 1a of the optical wave-guide and is conducted to the sample 4. Then the light is reflected by the total reflection on the sample 4 and is reflected on the inclined surface 1b. The reflected light exits from the optical wave-guide 1. In the embodiment illustrated in FIG. 4, the inclined surfaces 1a and 1b are used only for the reflection of the light. Alternatively, the sample 4 may be disposed on the inclined surfaces 1a and 1b. These inclined surfaces 1a and 1b as well as the bottom surface 3 may be intended to make the total reflection of light.

Figure 5:
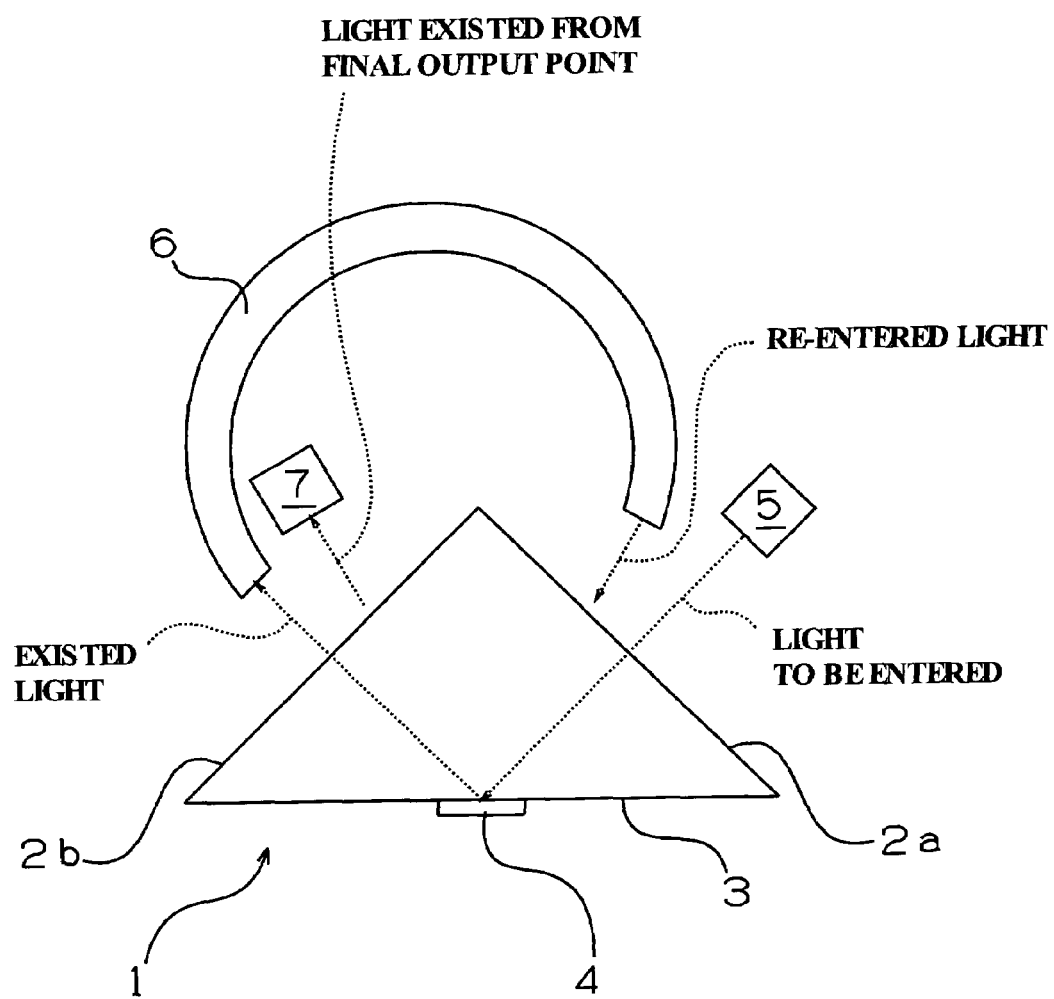
FIG. 5 is a schematic side view showing the fourth embodiment of the device for measuring the optical absorption characteristics of the sample according to the present invention.

Furthermore, the optical wave-guide is not necessarily the truncated shape. Alternatively, it may be a cone or pyramid shape (See FIG. 5).

In the above embodiment, input points and output points are positioned on the different surface, respectively. However, the positions of the input point and output point are not restricted to the above embodiment. For example, a matrix assembly of a number of optical fibers may be arranged such that a number of input points through which the light is entered and re-entered into the optical wave-guide from each of the optical fiber of the matrix are arranged on the same input surface and a number of output point through which the light exits and re-exits from the optical wave-guide are arranged on the same output surface.

FIGS. 6 to 9 show fifth embodiment of a device for measuring the optical absorption characteristics of the sample according to the present invention. The device for measuring the optical absorption characteristics has a matrix assembly that consists of four optical fibers. The matrix assembly is arranged between an input surface and an output surface of a prism 21 as an optical wave-guide, so that four input points are positioned on the same input surface of the prism 21 and four output points are positioned on the same output surface of the prism 21. In these drawings, numeral numbers 20a to 20e indicate optical fibers, and numeral number 22 indicates a reflecting surface of the prism, on which a sample being measured is disposed.

Figure 6:
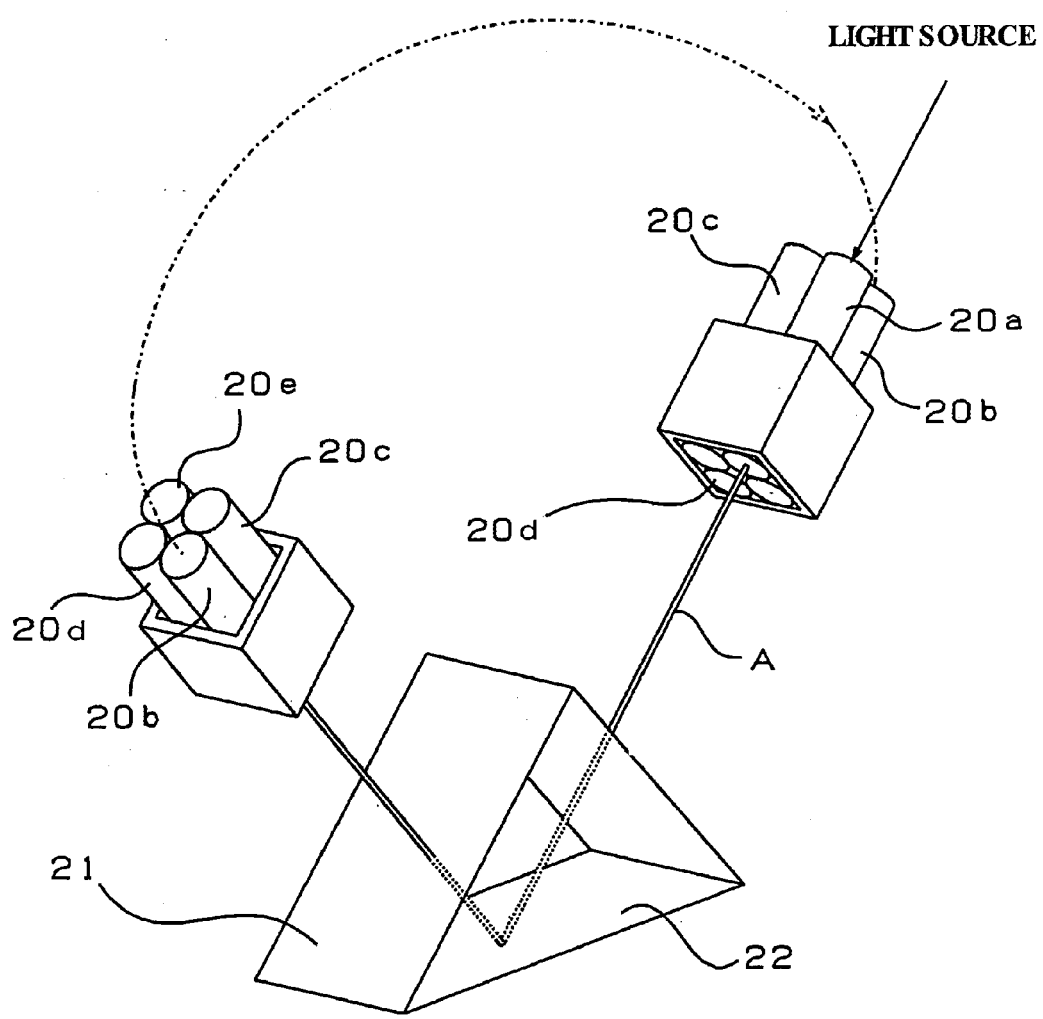
FIG. 6 is a schematic perspective view showing the fifth embodiment of the device for measuring the optical absorption characteristics of the sample according to the present invention.

As shown in FIG. 6, a light A from a light source is entered into the prism 21 through the optical fiber 20a, and then the light A is reflected by the total reflection on the sample of the reflecting surface 22. By way of the total reflection, the light A exits from the prism 21 and is received by the optical fiber 20b.

Figure 7:
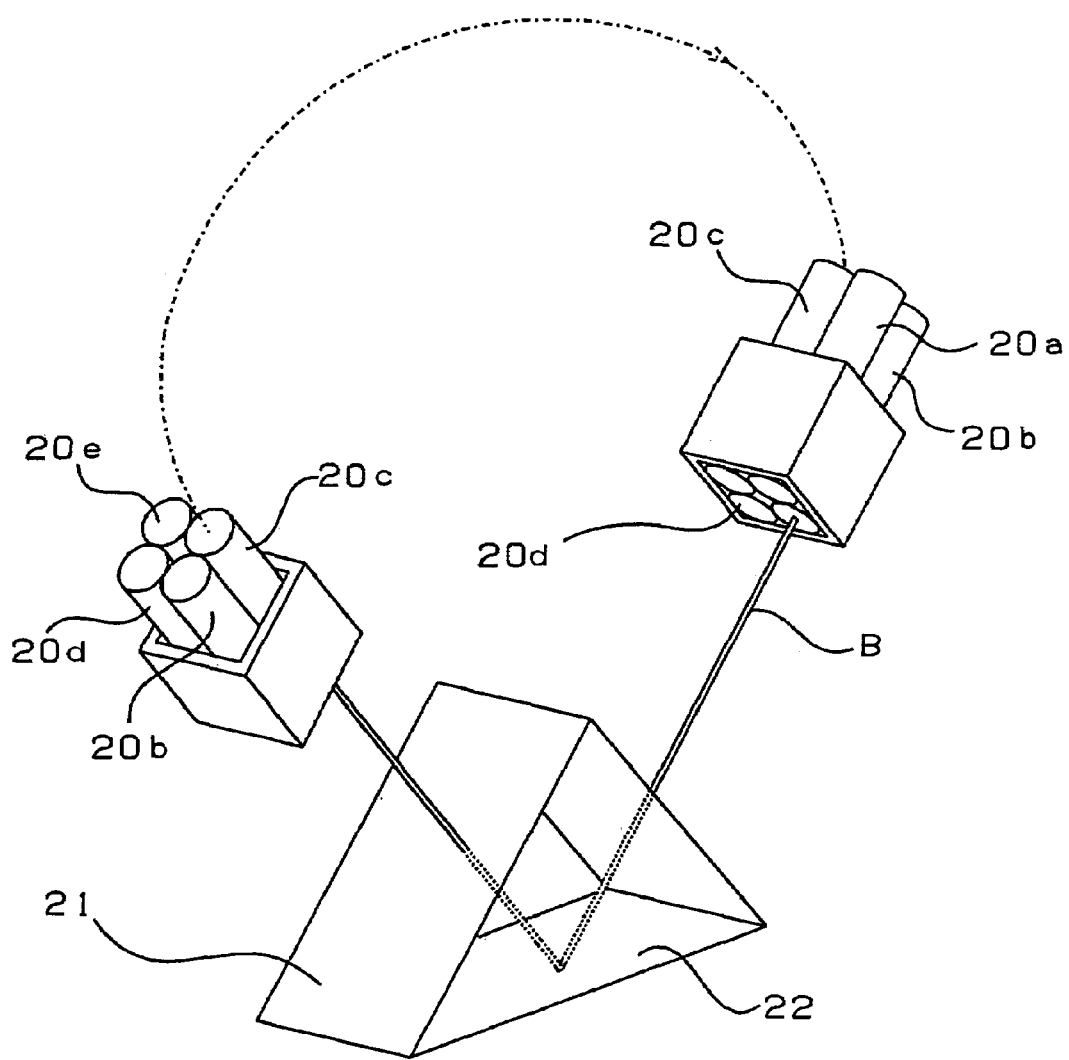
FIG. 7 illustrates the function of the device for measuring the optical absorption characteristics of the sample shown in FIG. 6.

As shown in FIG. 7, the optical fiber 20b transmits the light to the input surface of the prism 21. The light B from the optical fiber 20b is re-entered into the prism 21, and then the light B is re-reflected by the total reflection on the sample on the reflecting surface 22. By way of the total reflection, the light B re-exits from the prism 21 and is received by the optical fiber 20c. And the optical fiber 20c transmits the light to the input surface of the prism 21.

Figure 8:
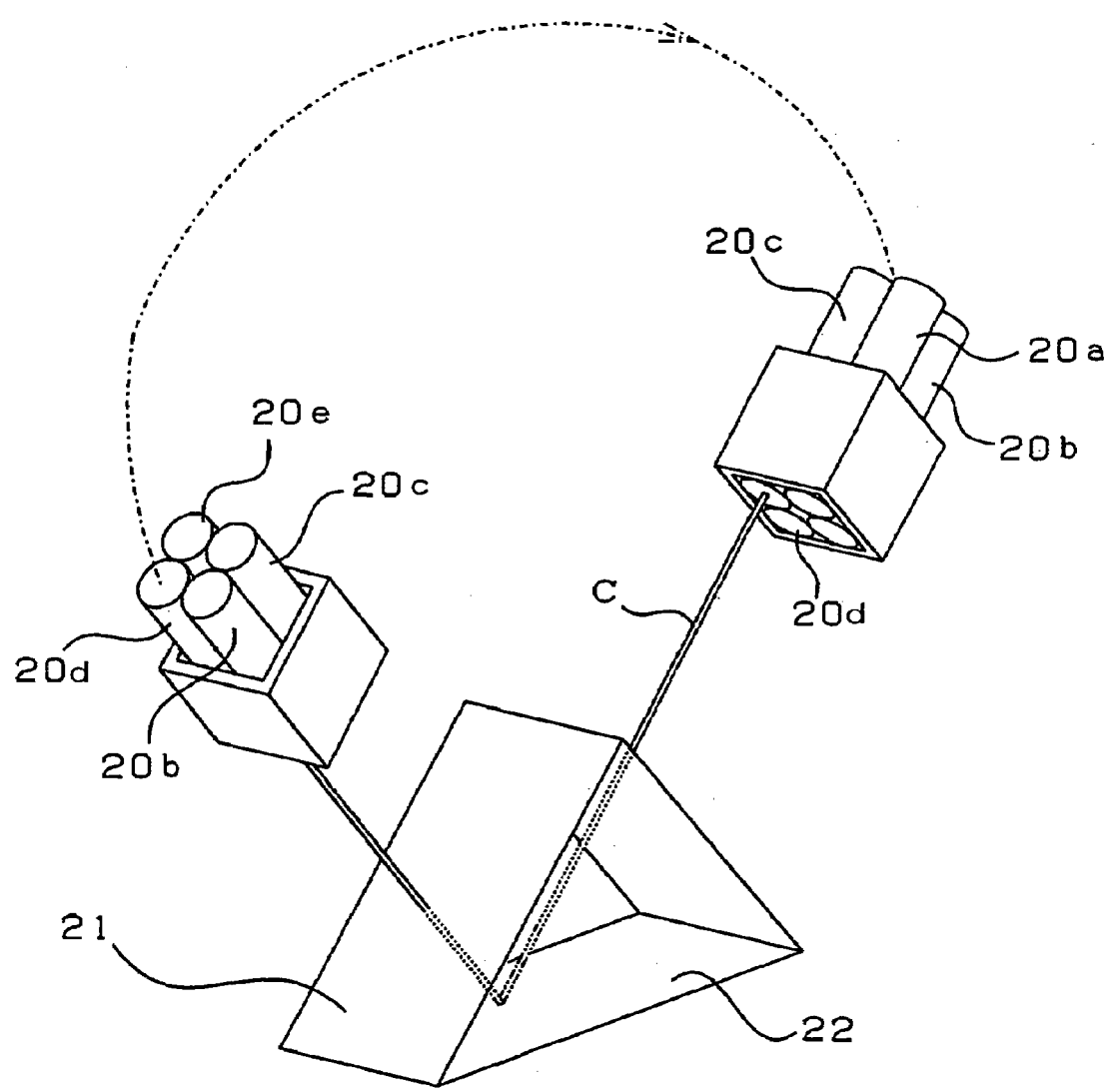
FIG. 8 illustrates the function of the device for measuring the optical absorption characteristics of the sample shown in FIG. 6.

As shown in FIG. 8, the light C from the optical fiber 20c is again entered into the prism 21, and then the light C is again reflected by the total reflection on the sample on the reflecting surface 22. After that, the light C re-exits from the prism 21 and is received by the optical fiber 20d. The optical fiber 20d transmits the light to the input surface of the prism 21.

Figure 9:
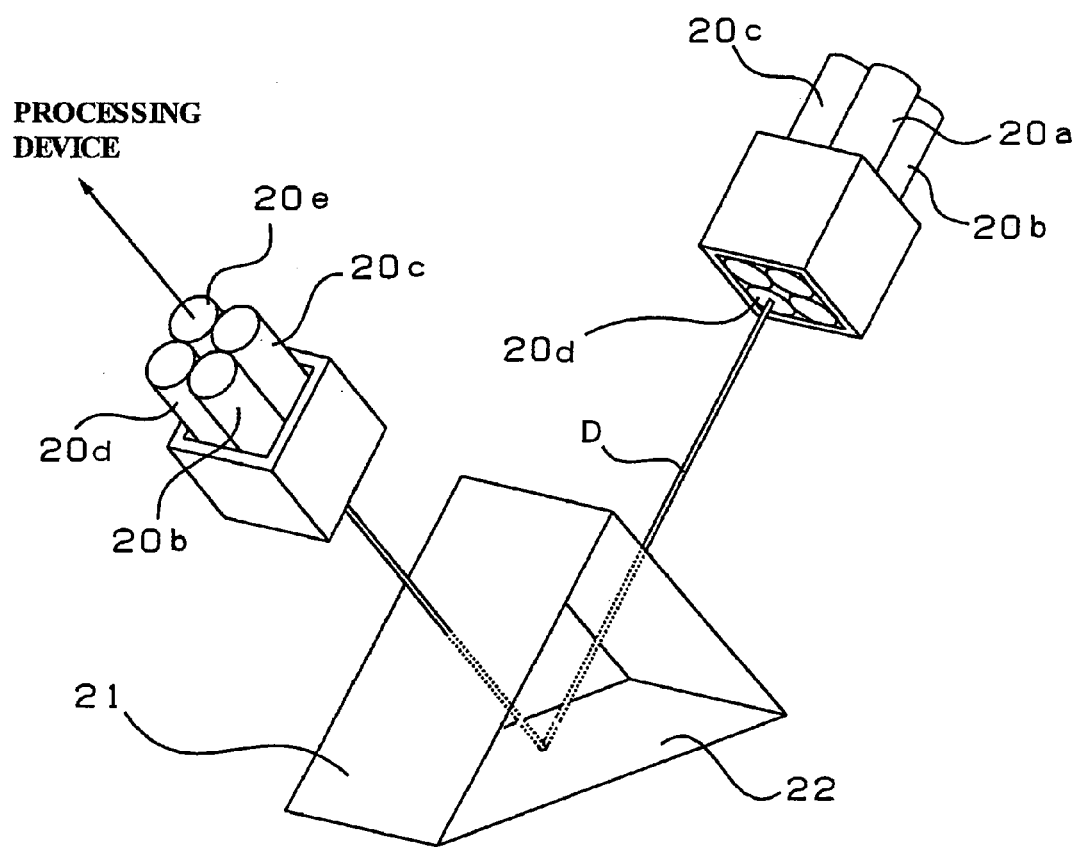
FIG. 9 illustrates the function of the device for measuring the optical absorption characteristics of the sample shown in FIG. 6.

As shown in FIG. 9, the light D form the optical fiber 20d is re-entered into the prism 21, and then the light D is re-reflected by the total reflection on the sample on the reflecting surface 22. After that, the light D re-exits from the prism 21, and is received by the optical fiber 20e. The optical fiber 20e is connected to a processing device not shown in drawing.

In the above embodiment, the matrix assembly consists of the four optical fibers. However the number of the optical fibers of the matrix is not restricted to the above embodiment. For example, the matrix assembly may be made from the one hundred optical fibers each of which has a diameter of 0.1 mm, so that the light may be reflected one hundred times on the sample within an area of 1 mm$^2$.

It is impossible to reflect the light at the same reflecting point in the above embodiment shown in FIGS. 6 to 9. However as shown in FIGS. 6 to 9, all reflecting points very closes each other, so that the size of the prism is smaller than the size of the prism used in the conventional optical absorption measuring device, and the amount of the sample required in the above mentioned device of the present invention is less than the amount of the sample required in the conventional measuring device.

It is possible to increase the number of the light reflecting times by combining the embodiment described in the FIG. 1 and the embodiment described in the FIGS. 6 to 9. More especially, for example, the optical wave-guide is truncated four-side pyramid, i.e. has two pairs of the input surface and output surface. And one matrix assembly made from the one hundred optical fibers each of which has a diameters of 0.1 mm is arranged between the first input surface of the optical wave-guide and the first output surface of the optical wave-guide, and other matrix assembly made from the one hundred optical fibers each of which has a diameters of 0.1 mm between the second input surface of the optical wave-guide and the second output surface of the optical wave-guide. By this construction, it is possible to reflect the light two hundred times on the sample within an area of 1 mm$^2$.

Figure 10:
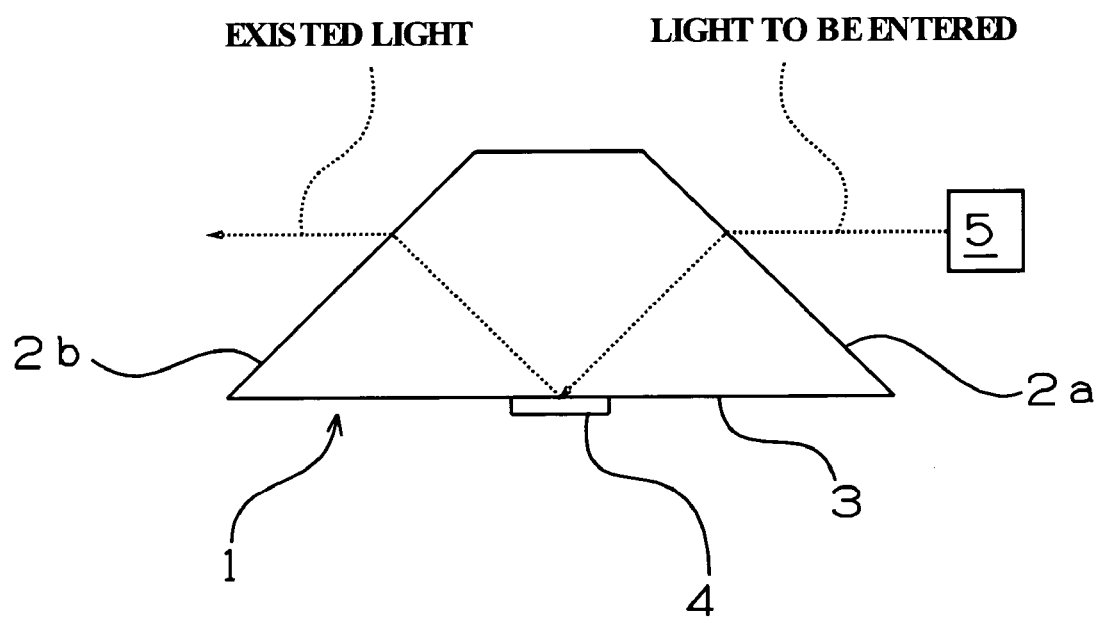
FIG. 10 is a schematic side view showing the sixth embodiment of the device for measuring the optical absorption characteristics of the sample according to the present invention.

In the above-mentioned embodiment, the light is perpendicularly entered with respect to the input surface and the light perpendicularly exits with respect to the output surface. However, the input angle and the output angle of the light is not restricted to the above embodiment, for example, as shown in FIG. 10 the light may be refracted by using the inclination of the input surface 2a and output surface 2b of the optical wave-guide 1 in order to direct the light to the sample 4.

The seventh embodiment of an device for measuring an optical absorption characteristics of a sample according to the present invention will be described with reference to the FIG. 11.

The same numeral number is put on the same element as the element of the above embodiments.

The device for measuring the optical absorption characteristics comprises housing 10 in which a light source 5, an optical fiber 6, and an optical receiving element 7 are provided.

The device for measuring the optical absorption characteristics also comprises an optical wave-guide in which a sample to be measured is disposed.

The optical fiber 6 transmits the light exited from the optical wave-guide to the optical wave-guide again, so that the light is re-entered into the optical wave-guide and the light is again reflected on the sample disposed on the optical wave-guide.

The device for measuring the optical absorption characteristics also comprises a processing device 11 that detects the optical absorption characteristics of the sample disposed on the optical wave-guide on the basis of the light that was reflected on the sample several times in the optical wave-guide, exits from the optical wave-guide, and then is received by the optical receiving element 7. The processing results of the processing device 11 are displayed on a display 12.

In the above-mentioned device for measuring the optical absorption characteristics, the light source 5, the optical fiber 6, the optical receiving element 7, the processing device 11, and the display 12 are provided in the housing 10, so that it is possible to provide an all-in-one portable type device for measuring the optical absorption characteristics that is novelty. The size of the all-in-one type portable device for measuring the optical absorption characteristics depends on the size of the optical wave-guide. The above device for measuring the optical absorption characteristics has the optical fiber 6 by which the light is returned from the output surface to the input surface of the optical wave-guide, so that the light is re-entered into the optical wave-guide and is re-reflected on the sample in the optical wave-guide. Therefore, at the one reflecting point or the closest points the light is reflected several time by the total reflection on the sample, so that the size of the optical wave-guide is very small. Therefore, the size of the device for measuring the optical absorption characteristics of the sample is also very small. And because of the device for measuring the optical absorption characteristics of the sample is all-in-one type, the optical absorption measuring device may be portable.

Figure 11:
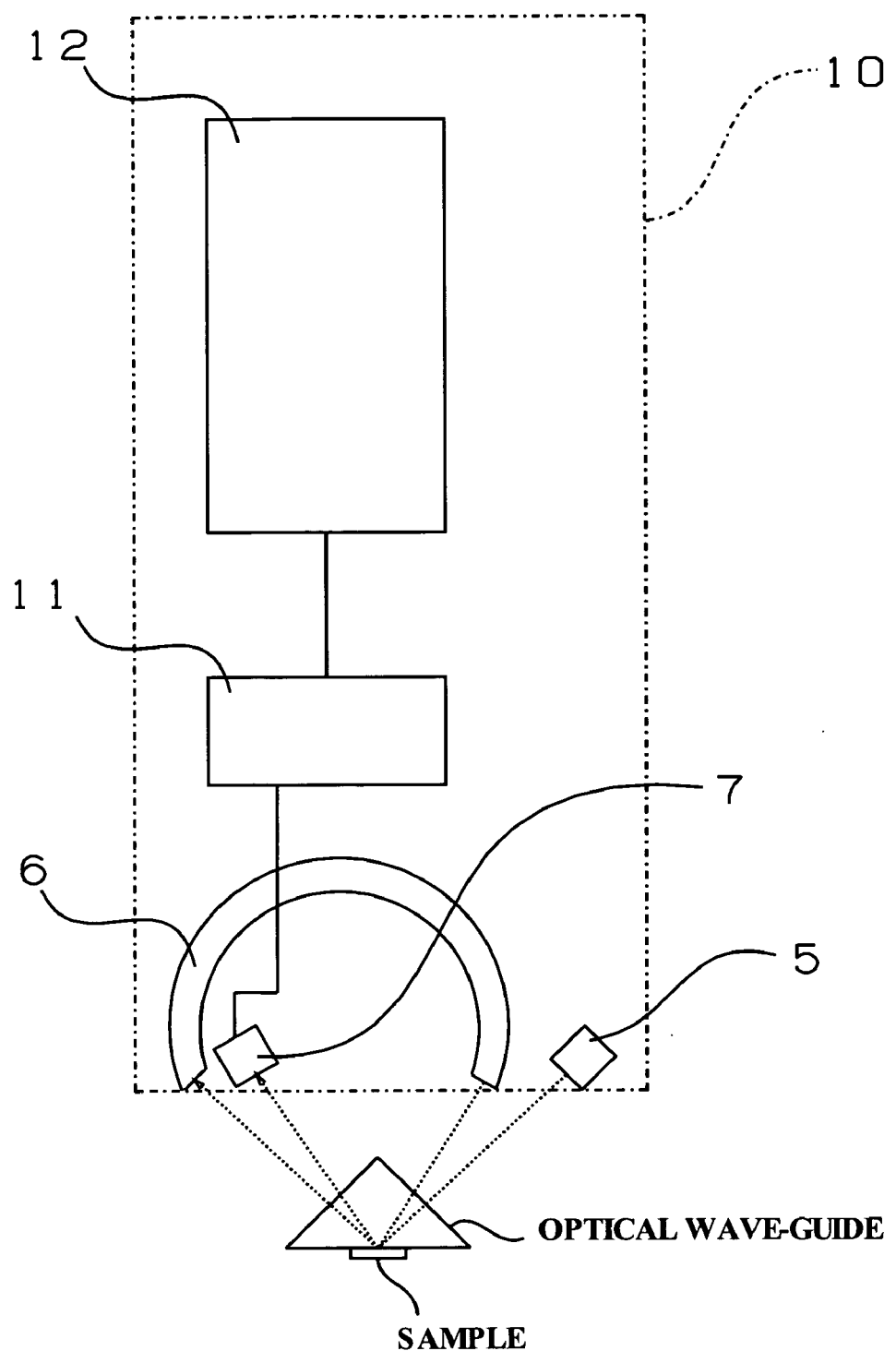
FIG. 11 is a schematic diagram showing the seventh embodiment of the device for measuring the optical absorption characteristics of the sample according to the present invention.
Figure 12:
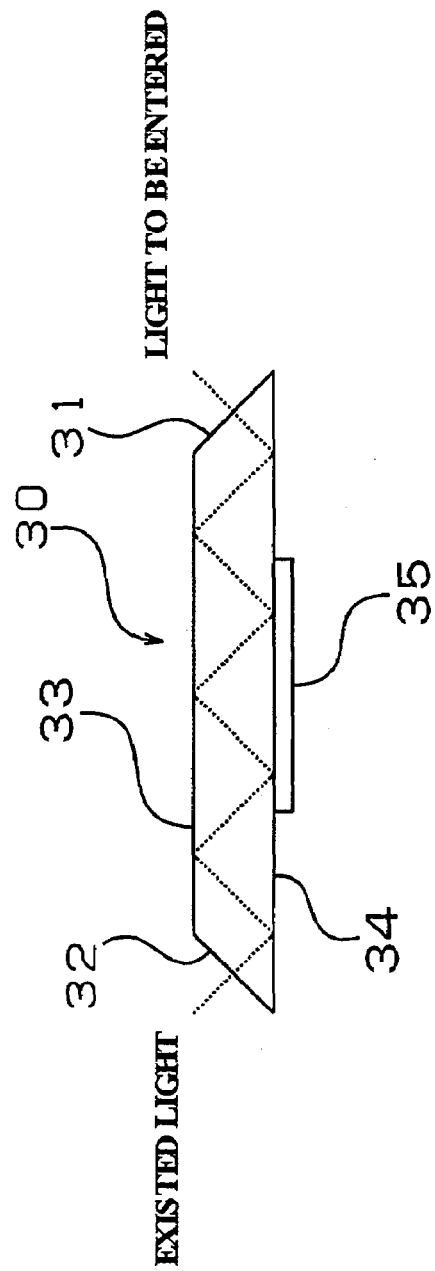
FIGS. 12(a) and 12(b) show the conventional optical wave-guides.
Figure 12:
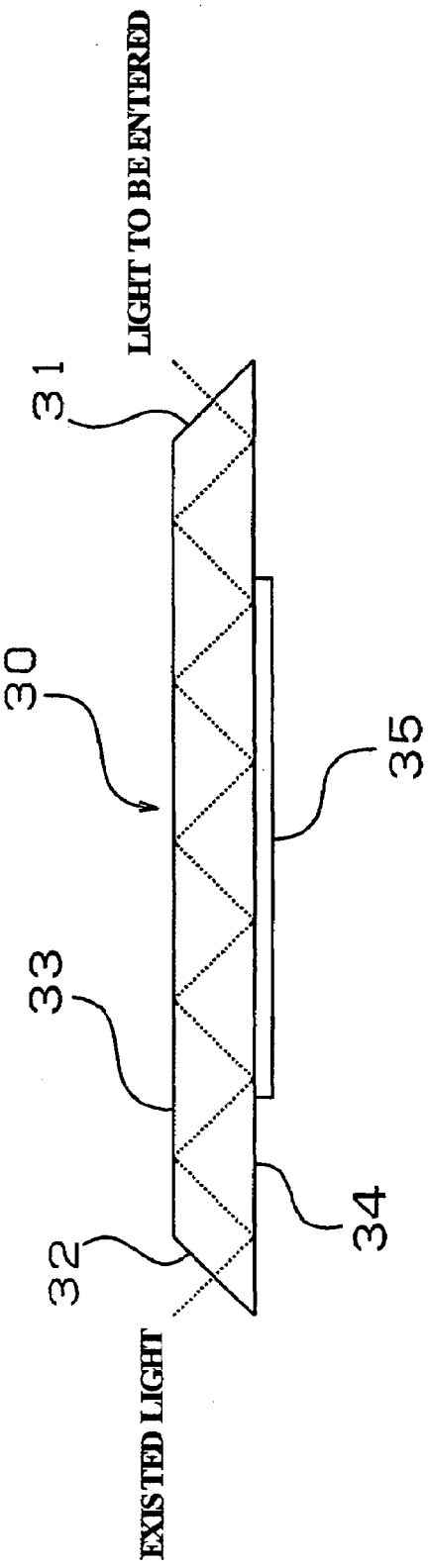

In the above embodiment shown in FIG. 11, the light source 5, the optical fiber 6, the optical receiving element 7, the processing device 11, and the display 12 are provided in one housing, however the construction of the device for measuring the optical absorption characteristics of sample is not restricted to the above-mentioned embodiment.

In the above embodiment shown in FIG. 11, the result is displayed with the display. However, the construction of the device for measuring the optical absorption characteristics according to the present invention is not restricted the above-mentioned embodiment, for example, the result may be output by using the printer, the any type of a storage media, a lump, or a speaker.

In the above embodiment shown in FIG. 11, the optical fiber is provided in the housing in order to return the light from the output surface of the optical wave-guide to the input surface of the optical wave-guide, so that the light is re-entered into the optical wave-guide. However, the construction of the light transmitting means is not restricted to the embodiment in FIG. 11. For example a matrix assembly of a number of the optical fibers may be provided in the housing in place of the optical fiber, so that a lot of reflection times may be obtained.

If necessary, the P-type light polarizer (longitudinal wave) or S-type light polarizer (transverse wave) may be provided between the optical fiber and the optical wave-guide, so that it is possible to detect the direction of the molecule in the sample arranged on the reflecting surface.

The invention claimed is:

1. A method of measuring optical absorption characteristics of a sample comprising conducting a light from a light source to a optical wave-guide that has light input surface(s) and light output surface(s) that are opposite to each other, and a reflecting surface on which a sample to be measured is disposed, through which the light passes and is reflected by a total reflection on the sample, transmitting the light exited from the optical wave-guide through the output surface thereof to the input surface of the optical wave-guide so that the light is again entered into the optical wave-guide at least one time, receiving the light re-exited from the optical wave-guide, and detecting the optical absorption characteristics of the sample on the basis of the light received.

2. The method of the measuring the optical absorption characteristics of the sample according to claim 1, wherein the optical absorption characteristics are at least any one of an amount of an optical absorption of the sample, an optical absorption spectrum of the sample, and an optical absorption intensity of the sample.

3. A device for measuring an optical absorption characteristic of a sample comprising a light source, a optical wave-guide having light input surface(s) and light output surface(s) that are opposite to each other, and a light reflecting surface on which a sample to be measured is disposed, through which the light passes and is reflected by a total reflection on the sample, one or more light transmitting means arranged between the light output surface of the optical wave-guide and the light input surface of the optical wave-guide so that the light is again entered into the optical wave-guide, and a processing device which receives the light re-exited from the optical wave-guide through the output surface and detects the optical absorption characteristics of the sample on the basis of the light received, whereby the light which passes through the optical wave-guide is conducted to the optical wave-guide again, the light is again entered the optical wave-guide, and the light is again reflected on the sample.

4. The device for measuring the optical absorption characteristics of the sample according to claim 3, wherein
the optical absorption characteristics are at least any one of an amount of the optical absorption of the sample, an optical absorption spectrum, and an optical absorption intensity.

5. The device for measuring the optical absorption characteristics of the sample according to claim 3, wherein
the light transmitting means comprises one or more optical fibers.

6. The device for measuring the optical absorption characteristics of the sample according to claim 3, wherein
the optical wave-guide has at least two pairs of the light input surface and the light output surface, the light input and output surfaces in each pair being opposite to each other,
the transmitting means transmits the light exited from the optical wave-guide through one output surface to other input surface that is not opposite to said output surface.

7. The device for measuring the optical absorption characteristics of the sample according to the claim 6, wherein
the light that enters again into the optical wave-guide through the one input surface is reflected on the sample at the same point of the reflecting surface of the optical wave-guide at which the light that enters or re-enters into the optical wave-guide through the other input surface is reflected.

8. The device for measuring the optical absorption characteristics of the sample according to claim 3, wherein
the optical wave-guide has one input surface and one output surface, the light is entered or re-entered into the optical wave-guide through the same input surface and the light exits or re-exits from the optical wave-guide through the same output surface.

9. The device for measuring the optical absorption characteristics of the sample according to claim 3, wherein the optical wave-guide is made from transparent material.

10. The device for measuring the optical absorption characteristics of the sample according to claim 3, wherein
the optical wave-guide is a pyramid shape having at least two pairs of the side surfaces that are opposite to each other.

11. The device for measuring the optical absorption characteristics of the sample according to the claim 10, wherein
the optical wave-guide is a truncated pyramid shape.

12. The device for measuring the optical absorption characteristics of the sample according to claim 3, wherein
the optical wave-guide is a conical shape.

13. The device for measuring the optical absorption characteristics of the sample according to the claim 12, wherein
the optical wave-guide is a truncated conical shape.

* * * * *